United States Patent [19]

Cummins et al.

[11] Patent Number: 5,081,010
[45] Date of Patent: Jan. 14, 1992

[54] EXTRACTION COMPOSITION, TEST KIT AND THEIR USE TO EXTRACT OR DETERMINE HERPES SIMPLEX VIRAL ANTIGEN

[75] Inventors: Thomas J. Cummins, Rochester; Sheryl S. Sullivan, Hilton, both of N.Y.; Randall D. Madsen, Pleasant Hill, Calif.; Nancy F. Green, Pittsford, N.Y.

[73] Assignees: Eastman Kodak Company, Rochester, N.Y.; Cetus Corporation, Emeryville, Calif.

[21] Appl. No.: 308,841

[22] Filed: Feb. 9, 1989

[51] Int. Cl.$^5$ .......................................... G01N 33/571
[52] U.S. Cl. ....................................... 435/5; 435/975; 435/961; 435/259; 252/117; 252/156; 252/548
[58] Field of Search ............... 435/5, 7, 810, 961, 435/975, 259; 436/518, 531, 533, 534, 808, 809, 810; 424/89, 43; 252/117, 156, 548; 530/395, 826

[56] References Cited

U.S. PATENT DOCUMENTS

| | | | |
|---|---|---|---|
| 4,430,437 | 2/1984 | Hampar et al. | 436/548 |
| 4,452,734 | 6/1984 | Larson et al. | 424/89 |
| 4,497,899 | 2/1985 | Armstrong et al. | 436/510 |
| 4,572,896 | 2/1986 | Hampar et al. | 435/172.2 |
| 4,661,349 | 4/1987 | Kino et al. | 424/89 |
| 4,695,537 | 9/1987 | Dorsett | 435/5 |
| 4,847,199 | 7/1989 | Snyder et al. | 435/36 |

FOREIGN PATENT DOCUMENTS

| | | |
|---|---|---|
| 001365 | 4/1979 | European Pat. Off. |
| 084013 | 7/1983 | European Pat. Off. |
| 172471 | 2/1986 | European Pat. Off. |
| 183215 | 6/1986 | European Pat. Off. |
| 183383 | 6/1986 | European Pat. Off. |

OTHER PUBLICATIONS

The Merck Index 10th ed., M. Windholz, editor 1983 pp. 541 and 1381.
Fucillo et al., "Rapid Viral Diagnosis" Manual of Clinical Laboratory Immunology 1986 pp. 489–496.
Zweig et al., *J. Virology* 47(1), pp. 185–192 (1983).

*Primary Examiner*—Esther L. Kepplinger
*Assistant Examiner*—Carol E. Bidwell
*Attorney, Agent, or Firm*—J. Lanny Tucker

[57] ABSTRACT

An extraction composition has been found useful for extracting antigen from herpes simplex virus. This composition has a pH of from about 8.5 to about 12, and comprises an alcoholamine or salt thereof, a nonionic surfactant comprised of a condensation product of an alkylphenol and ethylene oxide, cholic acid or a salt or derivative thereof and an anionic surfactant. Extraction of antigen is accomplished by contacting the extraction composition with a specimen suspected of containing herpes organisms under suitable conditions. Extracted antigen can be determined by forming an immunological complex with antibodies thereto and by detecting that complex. The extraction composition can be supplied as part of a diagnostic test kit.

24 Claims, No Drawings

EXTRACTION COMPOSITION, TEST KIT AND THEIR USE TO EXTRACT OR DETERMINE HERPES SIMPLEX VIRAL ANTIGEN

FIELD OF THE INVENTION

This invention relates to an extraction composition and its use to extract and determine herpes simplex viral antigen. It also relates to a diagnostic test kit including the extraction composition. The present invention is useful in diagnostic procedures to detect herpes simplex virus in biological specimens.

BACKGROUND OF THE INVENTION

Immunoassays have been used in recent years to detect the presence of infectious diseases. In order for the assay to be useful, it must detect a particular organism with a high degree of reliability. In most cases, this requires the isolation and reaction of antigens peculiar to the organism with corresponding antibodies. For the test to be commercially successful, it also needs to be relatively inexpensive, simple to use and rapid.

One such organism which can be detected by immunoassay is herpes simplex virus. Despite the increasing control of various viruses by vaccination or treatment with various anti-viral agents, infection by herpes simplex virus (identified herein as HSV) remains a serious problem. There are two types of HSV: type 1 which occurs mainly around the mouth, and type 2 which occurs primarily around the genital area of the human body. Skin infections and viral encephalitis are but two of the serious results from HSV infection.

Because of the widespread nature of herpes infection, there is considerable interest in having a rapid, simple and reliable test for detection of the causative virus. However, there are several similar viruses which often are indistinguishable from HSV using known diagnostic procedures. Thus, a useful diagnostic test for HSV-1 or HSV-2 must be specific for these viruses only, and must not be sensitive to viruses such as Epstein-Barr virus, cytomegalovirus, varicella zoster virus or any other flora.

Extraction of antigen from the organisms in a biological specimen is critical to providing an accurate, rapid and sensitive assay. Many varied techniques have been used for extraction including physical disruption of the cells by sonication, heating or centrifugation. Chemical extraction compositions have also been developed. For example, U.S. Pat. No. 4,661,349 (issued Apr. 28, 1987 to Kino et al) describes the extraction and purification of a 90,000-95,000 dalton molecular weight glycoprotein B from HSV in the preparation of a vaccine. Extraction is accomplished using any of a number of nonionic or anionic surfactants at neutral pH.

U.S. Pat. No. 4,430,437 (issued Feb. 7, 1984 to Hampar et al) describes extraction of nucleocapsid proteins from HSV using first a mixture of glycerol, Nonidet P-40 nonionic surfactant, sodium deoxycholate and phenylmethylsulfonylfluoride at pH 8, followed by treatment with sodium dodecyl sulfate, a mercaptoethanol at pH 8 and 100° C. It is to be noted that the low pH and high temperature are important for the described extraction procedure.

Ethanolamine has been used in combination with surfactants and high temperature heating (for example, 70°-110° C.) to extract chlamydial antigens at a pH below 8 as described in E.P. Publication 183,383 (IQ BIO).

There is a need in the art for a means of extracting herpes simplex viral antigen to provide sensitive and rapid assays that can be readily adapted to simple test devices.

SUMMARY OF THE INVENTION

The present invention provides an extraction composition useful for extracting antigen from herpes simplex virus, the composition having a pH of from about 8.5 to about 12, comprising an alcoholamine or a salt thereof, a nonionic surfactant comprised of a condensation product of an alkyl phenol and ethylene oxide, cholic acid or a derivative or salt thereof and an anionic surfactant.

Further, a method for extracting an antigen from herpes simplex virus comprises:

A. providing a specimen suspected of containing herpes simplex virus, and

B. contacting the specimen with the extraction composition described above.

This invention also provides a method for the determination of herpes simplex virus comprising:

A. extracting herpes simplex viral antigen from a specimen suspected of containing herpes simplex virus with the extraction composition described above, B. contacting the extracted antigen with antibodies thereto to form an immunological complex, and C. determining the presence of the complex as an indication of the presence of herpes simplex virus in the specimen.

Further, a diagnostic test kit useful for the determination of herpes simplex virus comprises:

(a) the extraction composition described above, and (b) antibodies directed to a herpes simplex viral antigen.

In a preferred embodiment, the herpes simplex viral antibodies used in the invention are monoclonal antibodies derived from hybridoma cell line 283-2A1-1D4-2C3 deposited as HB-9684 with the American Type Culture Collection in Rockville, Maryland.

The extraction composition of this invention rapidly and effectively lyses HSV or HSV-infected cells in a biological specimen to release sufficient antigen for a sensitive assay. Lysis can be carried out very quickly, usually in less than about 2 minutes, and at room temperature using standard equipment. High temperature extraction procedures are thereby avoided. The operator skills required are not unusual. HSV is effectively detected with the present invention using an extraction composition and procedure which does not destroy epitopic sites of interest and in which interfering substances are removed.

It has also been found that the assay of this invention can be effectively carried out using solid supports (such as microporous membranes) and a simple test device. Unlike assays using known extraction compositions, the present invention provides a rapid separation of soluble and insoluble materials using the test device.

These advantages are achieved because of the use of the particular extraction composition of this invention which is buffered to high pH (about 8.5 to about 12), and contains a critical combination of an alcoholamine or a salt thereof, a particular nonionic surfactant, cholic acid or a derivative or salt thereof and an anionic surfactant. In preferred embodiments, a particularly useful optional component of the composition is an inorganic salt. These materials are described below. A composition containing less than the required materials is ineffective to provide desired results (see Example 3 below).

DETAILED DESCRIPTION OF THE INVENTION

The present invention includes an extraction composition and method, as well as a method for determining the presence of HSV in a biological specimen which has been obtained from a patient using standard medical and microbiological techniques. Biological specimens include, for example, swab specimens obtained from the cervix, urethra, eyes, throat or anus of a patient, and body fluids such as synovial fluid or fluid from lesions. The biological specimens so obtained are suspected of containing HSV or HSV-infected cells which contain the antigen to be determined.

While some assays in the art are designed to detect whole virus infected cells, it is an advantage of this invention that the viruses or virus-infected cells or membranes are effectively lysed and sufficient antigen extracted to provide a sensitive assay in a relatively short period of time. Antigens can be extracted from infected whole host cells or cell membranes, or from virions present in the sample.

The antigens detectable with the present invention are present in either HSV-1 or HSV-2 or both. Antigens of the virions are extracted and detected with the present invention. In particular, the glycoprotein antigen is readily extracted and detected with the present invention.

The extraction composition of this invention has a pH of from about 8.5 to about 12, and preferably of from about 9 to about 11. The desired pH can be obtained using appropriate buffers or bases. Some buffers are strong enough bases to provide the alkaline conditions as well as the buffering capacity. Other buffers are not, and a strong base (such as a hydroxide like sodium hydroxide or potassium hydroxide) is used to obtain the pH, and the buffer is then used to maintain that pH. For example, when a salt of ethanolamine is used as a buffer, a strong base is useful to obtain a pH about 9.5.

The composition comprises one or more alcoholamines or salts thereof in an amount of at least about 0.05, and preferably from about 0.1 to about 1, molar. Useful alcoholamines include ethanolamine, diethanolamine, propanolamine, triethanolamine and salts thereof (such as hydrochlorides, sulfates, acetates, picrates and oxalates). Others would be readily apparent to one skilled in the art. Mixtures of alcoholamines or salts thereof can be used if desired. Ethanolamine or a salt thereof is particularly preferred.

The composition also includes one or more nonionic surfactants which are condensation products of an alkylphenol and ethylene oxide. Preferred alkylphenols have from 1 to 20 carbons in the linear or branched alkyl group on the phenol. Octylphenol is most preferred. Generally, these compounds have from 5 to about 35 ethylene oxide groups. Preferably, they have from 7 to 15 ethylene oxide groups. These nonionic surfactants are readily prepared using known procedures and starting materials, but many are also commercially available. A most preferred surfactant is marketed under the tradename of NONIDET P-40 (Calbiochem).

Other useful nonionic surfactants include, but are not limited to, polyoxyethylene ethers such as those sold under the TRITON TM mark (Rohm and Haas), for example TRITON TM X-100 and TRITON TM N101 nonionic surfactants, or under the BRIJ tradename (from ICI Americas, Inc.), polyoxyethylenesorbitan derivatives, such as those sold under the TWEEN tradename (for example TWEEN-20 nonionic surfactant from ICI Americas, Inc.), and polyglycol ethers such as those sold under the TERGITOL tradename (for example TERGITOL NPX and NP-7 nonionic surfactants from Union Carbide). Other useful materials would be readily apparent to one skilled in the art, especially after consulting the standard reference for surfactants, *McCutcheon's Emulsifiers and Detergents*, 1986 Edition, McCutcheon Division, Publishing Co., Glen Rock, N.J.

One or more of the nonionic surfactants are present in the extraction composition in an amount of at least about 1, and preferably from about 4 to about 10, weight percent (based on total composition weight).

A third critical component of the extraction composition of this invention is one or more of cholic acid, a salt or derivative thereof. Useful materials include, but are not limited to, cholic acid, chenodeoxycholic acid, deoxycholic acid, sodium deoxycholate, potassium chenodeoxycholate, ammonium cholate and others readily apparent to one skilled in the art. Most preferred is sodium deoxycholate. This component is present in the composition in an amount of at least about 0.2, and preferably from about 0.5 to about 5, weight percent (based on total composition weight).

The extraction composition also includes an anionic surfactant in an amount of at least about 0.1, and preferably from about 0.2 to about 1, weight percent (based on total composition weight). Useful anionic surfactants include, but are not limited to, water soluble or dispersible compounds comprising an alkyl sulfate anion and an alkali metal (for example, lithium, sodium or potassium) or ammonium cation, the alkyl having from about 6 to 20 carbon atoms. Preferably, the alkyl has from 6 to 12 carbon atoms (such as linear or branched hexyl, octyl, decyl, 2-methylhexyl and dodecyl groups). Arylsulfonic acids or salts thereof (as described above) having from 6 to 10 carbon atoms in the aryl nucleus would also be useful. Alkyl sulfates are preferred with decyl and dodecyl sulfates being most preferred. Representative anionic surfactants include ammonium dodecyl sulfate, sodium dodecyl sulfate, rubidium dodecyl sulfate, sodium decyl sulfate, lithium hexyl sulfate, potassium octyl sulfate and lithium decyl sulfate. Most preferred compounds are sodium decyl sulfate and sodium dodecyl sulfate.

An important, but optional, component of the extraction composition is one or more inorganic salts, such as alkali metal, ammonium or alkaline earth salts. Representative salts includes, but are not limited to, sodium chloride (which is most preferred), potassium chloride, ammonium chloride, calcium chloride, ammonium sulfate, barium sulfate and others readily apparent to one skilled in the art. The salt is preferably present in an amount of at least about 0.3, and more preferably from about 0.5 to about 2, molar.

Other addenda can be included in the extraction composition if desired, including preservatives, reducing agents, chelating agents and anti-foaming agents.

Extraction can be carried out by providing a biological specimen suspected of containing HSV or HSV-infected cells and contacting it with the extraction composition of this invention in a suitable container for enough time to lyse the virus or cells containing same and extract the antigen for the assay. Generally, the extraction procedure takes less than 2 minutes although a longer time may be desired with certain specimens. Contact is generally carried out at room temperature (that is, from 18° to 25° C.), but higher temperatures up to about 40° C. may be used if desired. However, the higher temperatures required in the art can be avoided by practicing this invention. Agitation of the specimen may be desirable. Preferably, extraction is carried out in a suitable extraction device which may be designed specially for that purpose. A number of such devices are shown in the art, such as in U.S. Pat. No. 4,746,614 (issued May 24, 1988 to Devaney, Jr. et al).

After suitable incubation, the solution containing extracted antigen can be neutralized with a suitable acid to reduce the pH to between 6 and 8, if desired. It may also be treated to remove endogenous peroxides. Once the antigen is extracted from the organisms, it is desirable, although not essential, that the noted solution be prefiltered to remove cellular debris, particulate matter and other unwanted materials prior to further handling. Prefiltering can be carried out in a suitable container having a filter of some type.

The filtered specimen is then subjected to any of a number of analytical procedures in order to determine the presence of extracted antigen. Such procedures include culture techniques, counter-immunoelectrophoresis and serological tests which, while not preferred, may be the only choice in certain instances.

Preferably, the extracted antigen is detected using an immunoassay in which it is immunologically reacted with one or more appropriate antibodies. Antigen from either or both of HSV-1 or HSV-2 can be detected. Preferably, both are detected simultaneously. The resulting immunological complex between extracted antigen and antibodies is detected using a suitable radiometric, colorimetric, fluorometric or enzyme labeled reagent. In some cases, the reagent is a labeled antibody to the antigen, and in other cases, a labeled anti-antibody is directed to an unlabeled antibody which is reactive with the antigen. Such immunoassays generally include the formation of a detectable immunological complex which is separated from uncomplexed materials in a suitable manner. In preferred embodiments, the complex is immobilized on a solid support of some type, either coated or uncoated, followed by appropriate detection procedures. Other assays involve agglutination of the immunological complex when at least one reactant (such as an antibody) of the complex is attached to labeled or unlabeled particles of some type that clump together during complex formation. An agglutination assay is illustrated in E.P. Publication 183,215 (published June 4, 1986).

Examples of useful assays include competitive immunoassays, radioimmunoassays (including radioimmunoprecipitation) or enzyme-linked immunoabsorbent assays (or what is commonly called "ELISA"). Procedures for such assays are described generally in U.S. Pat. No. 4,430,437 (issued Feb. 7, 1984 to Hampar et al) and in other art too numerous to mention. The HSV antibodies used can be directed to either or several antigens being extracted from the organisms. In one embodiment, antibodies are directed to a single glycoprotein of either HSV-1 or HSV-2. In other embodiments, a mixture of different antibodies is directed to several antigens, such as glycoproteins from both HSV-1 and -2. In still a third and preferred embodiment, a single antibody is used which is reactive with specific glycoproteins from both HSV-1 and -2.

The antibodies used in this assay can be polyclonal or monoclonal which can be purchased or prepared using known procedures. Preferred antibodies are monoclonal and reactive with glycoproteins from both HSV-1 and -2. One such monoclonal antibody is obtained using standard procedures from hybridoma cell line 283-2A1-1D4-2C3 (ATCC deposit HB-9684).

A useful solid phase immunoassay is described in copending U.S. Ser. No. 308,843 filed on even date herewith by Sutton, Cummins and Green and entitled "Method and Kit for Determination of Herpes Simplex Viral Antigen by Direct Binding to Polymeric Particles". In this embodiment, the extracted antigen is "captured" (or bound to) on small polymeric particles by absorption or by covalent reaction with reactive groups on the particles which react with free amine or sulfhydryl groups. Captured antigen is then reacted with the appropriate antibodies to form a bound immunological complex. Uncomplexed materials are separated using a microporous membrane filter described in more detail in the noted copending application.

A preferred immunoassay is carried out by binding extracted antigen on a coated or uncoated microporous membrane filter which is also used for separation of uncomplexed materials from the resulting immunological complex. The use of one such membrane to detect chlamydial or gonococcal antigen is described and claimed in copending U.S. Ser. No. 255,923 filed on Oct. 7, 1988 by Pronovost. Another immunoassay is carried out using a surfactant-coated microporous membrane similar to the chlamydial and gonococcal assays described in copending U.S. Ser. No. 255,920 filed on Oct. 7, 1988, by Mauck now U.S. Pat. No. 5,032,504 issued July 16, 1991. Both of these applications are incorporated herein by reference for the description of useful membranes and analytical procedures. Most preferably, the microporous membrane is an uncoated or untreated nylon material as shown in Example 2 below.

Generally, the assay of this invention using a solid support of some type (preferably a membrane or particles as described above) is carried out as follows. The extracted antigen is contacted with a solid support such as a glass, cellulosic, ceramic or polymeric material. Preferably, this support is constructed of any natural or synthetic polymeric material to which extracted antigen will bind rapidly and without undue incubation or other conditioning. Useful polymers include polyesters, polyamides, polycarbonates, polyethleneimines, cellulosic materials and addition polymers prepared from ethylenically unsaturated vinyl monomers and others known in the art. Generally, if the membrane is positively charged, the cationic groups are quaternary ammonium salts, quaternary phosphonium salts, quaternary sulfonium salts, quaternary pyridinium salts, quaternary pyrimidinium salts or quaternary imidazolium salts, with quaternary ammonium salts being preferred.

One preferred embodiment is the use of particles on a microporous membrane and capture of extracted antigen with the membrane and particles as described above.

The support can be configured in any suitable form, such as beads, gels, films or membranes. A microporous membrane is preferred as described herein.

The support described herein can be used in combination with other equipment (bottles, test tubes, swabs, beakers or cups) in order carry out the assay. Alternatively and preferably, the support is a microporous membrane which is fitted into a disposable test device in which the assay can be carried out and all fluids accommodated. Useful configurations of test devices are known in the art including U.S. Pat. Nos. 3,825,410 (issued July 23, 1974 to Bagshawe), 3,888,629 (issued June 10, 1975 to Bagshawe), 3,970,429 (issued July 20, 1976 to Updike) and 4,446,232 (issued May, 1984 to Liotta). Particularly useful devices are described and claimed in E.P. Publication 280,558 (published Aug. 31, 1988) and in 98,248 (filed Sept. 18, 1987 by Hinckley now abandoned).

Almost immediately upon contact of the antigen with the support, the antigen is bound to it. Binding may be by direct means referring to the antigen not being bound through a linking biological compound (such as an antibody) which is attached to the support, or binding may be indirectly through such linking compounds.

Therefore, within about 10 minutes, and preferably within 10 to 120 seconds, of the contact, bound antigen is contacted with suitable antibody (or mixture thereof) thereto so as to form an immunological complex on the support. If the assay is carried out using a disposable test device, the support can be a microporous membrane through which fluid and uncomplexed materials in the specimen are allowed to flow through as the antigen is bound to the membrane.

In a preferred embodiment, the antibody to the antigen is labeled for detection. Useful labels are known in the art and include chemical or biological compounds which are directly or indirectly detectable using suitable procedures and equipment, as well as compounds which can be detected through further chemical or specific binding reactions to provide a detectable species. Examples of useful labels include radioisotopes, enzymes, coenzymes, fluorescent compounds, cofactors, chemiluminescent compounds, phosphorescent compounds, biotin or its derivatives, avidin or its derivative, ferritin, magnetizable particles, dyed particles and others readily apparent to one skilled in the art. Radioisotopes or enzymes are preferred labels. The labels can be attached to antibodies using known techniques. Where the label is not directly detectable, further reagents or compounds are needed to render the reaction or specific binding product detectable. For example, if the label is biotin, it can be reacted with avidin which is conjugated with an enzyme to provide a detectable species. Where the label is an enzyme, such as glucose oxidase, urease, peroxidase, alkaline phosphatase and others, substrates and dye-providing reagents are also needed. Peroxidase and alkaline phosphatase are particularly useful.

In a particularly preferred embodiment, the label is peroxidase, and at some point in the assay, hydrogen peroxide and suitable dye-forming reagents are added to provide a detectable dye. For example, useful dye-providing reagents include tetramethylbenzidine and derivatives thereof, and leuco dyes, such as triarylimidazole leuco dyes (as described in U.S. Pat. Nos. 4,089,747, issued May 16, 1978 to Bruschi), or other compounds which react to provide a dye in the presence of peroxidase and hydrogen peroxide (that is, compounds which react to provide a dye upon catalytic action of peroxidase).

In another embodiment, the herpes antibody is not labeled, and detection of the antibody-antigen complex formed and bound to the support is accomplished using a second antibody (described below) which is specific to the HSV antibody and appropriately labeled (as described above) for detection.

The antibodies used in the assay can be supplied in admixture with one or more blocking proteins which reduce nonspecific interactions on the support. Useful proteins are well known and include, for example, casein, $\alpha$-casein, fetal bovine serum and porcine gamma globulin. One useful blocking composition comprises a nonimmunological blocking protein and an amphoteric surfactant.

To hasten the formation of the immunological complex bound to the support, the antibody and antigen are generally incubated at a temperature of from about 15° to about 30° C. for up to 10 minutes. Preferably, the incubation is at room temperature (i.e. from 18° to 25° C.) for up to 5 minutes.

After the incubation and within about 10 minutes of the antibody-antigen contact, the bound complex is washed one or more times with a buffered wash solution, such as a phosphate buffer, buffered solution of a nonionic surfactant (for example, that marketed under the tradename TWEEN 20) and other which are known in the art. A particularly useful wash solution is described and claimed in copending U.S. Ser. No. 308,844 filed on even date herewith by Cummins and Sullivan and entitled "Wash Composition, Test Kit and Their Use to Determine a Herpes Simplex Viral Antigen." This wash solution has a high pH and advantageously lowers background of the assay.

In the embodiment described above where the HSV antibody is labeled, the assay procedure after washing is to detect the label directly or indirectly after addition of the appropriate reagents. This is done relatively quickly after washing the bound complex. If desired, label detection can be hastened with incubation if the reagents warrant it. The label is then detected using standard equipment and procedures after a suitable time.

Where the HSV antibody is unlabeled, after washing the bound complex, it is contacted with an antibody directed to the unlabeled antibody. This second antibody (that is, an anti-antibody) is appropriately labeled with any of the labels described above, and can be supplied with a blocking composition as described above. The antibody can be monoclonal or polyclonal and either purchased or prepared using known techniques.

After this contact, the resulting antigen-antibody-antibody complex which is bound to the support is incubated for up to about 10 minutes at a temperature of from about 15° to about 30° C. Preferably, the incubation is at room temperature for up to about 5 minutes.

Further washing is carried out to remove uncomplexed materials, and suitable enzyme substrates or other needed reagents are added to provide a detectable species. The bound antigen-antibody-labeled antibody complex is then detected on the support using standard radiometric, colorimetric, fluorescent or other detection techniques.

The extraction composition of this invention can be supplied, if desired, as part of a diagnostic test kit which also comprises one or more other reagents, pieces of diagnostic equipment or other useful materials. Generally, the kit includes at least antibodies (labeled or unlabeled) directed to a herpes simplex viral antigen. It can also include, anti-antibodies (if needed), wash solutions, extraction devices, test devices, dye-providing reagents or compositions, pipettes, instructions, swabs and any other useful components for carrying out the assay. The components can be packages in any suitable manner and provided in one or more packages or containers.

The following materials, compositions and solutions were used in the examples below, which examples are provided to illustrate, but not limit the scope of, the present invention.

ANTIBODY PREPARATION

Hybridoma cells producing monoclonal antibodies to HSV were prepared using known procedures described by Köhler et al (*Nature*, 256, pp. 495-497, 1975). A hybridoma cell line was generated which produced a monoclonal antibody reactive to an epitope on a glycoprotein antigen common to both HSV-1 and HSV-2. The hybridoma cell line has been deposited as ATCC HB-9684.

ANTIGEN PREPARATION

To prepare the antigen for use as the positive control, HSV-1 strain F and HSV-2 strain G were grown separately in HEP-2 cells (ATCC CCL-23). The infected cells were pelleted by low speed centrifugation, and the pellets were resuspended to a volume of 15 ml in phosphate buffered saline in a 50 ml Corex tube. The resuspended cells were sonicated, exposed to aminomethyltrioxsalen (500 mg/ml) for 15 minutes, followed by ultraviolet irradiation for 15 minutes under constant stirring.

The positive control well of the test devices contained HSV-1 and HSV-2 antigens (UV inactivated and detergent lysed), incorporated on the filter membrane of the test well in admixture with bovine serum albumin (0.1 weight %) and a hydrophilic polymer (5 weight %).

ANTIBODY CONJUGATE PREPARATION

Monoclonal antibodies to HSV (described above) were conjugated to horseradish peroxidase (Miles Laboratories) using the method described by Yoshitake et al, *Eur. J. Biochem.*, 101, 395 (1979). The resulting conjugate was mixed with a blocking composition containing α-casein (0.5 weight %, Sigma Chemical Co.), TWEEN 20 nonionic surfactant (0.1 weight %, Sigma Chemical), thimerosal preservative (0.01 weight %) and p-methoxyphenol (100 mmolar), then sterile filtered. The final antibody concentration in this solution was 1.5 μg/ml. It was stored with bovine serum albumin (1 weight %). The conjugates for the negative control wells of the test devices were peroxidase labeled antibodies to creatine kinase, prepared using the procedures described above.

LEUCO DYE-PROVIDING COMPOSITION

This composition contained hydrogen peroxide (10 mmolar), 2-(4-hydroxy-3-methoxyphenyl)-4,5-bis(4-methoxyphenyl)imidazole leuco dye (0.005 weight %), poly(vinyl pyrrolidone) (1 weight %), 4'-hydroxyacetanilide (5 mmolar) and diethylenetriaminepentaacetic acid (10 mmolar).

HYDROGEN PEROXIDE SOLUTION

An aqueous solution was prepared containing hydrogen peroxide (10 weight %), diethylenetriaminepentaacetic acid (0.005 weight %) and preservative (0.01 weight %).

WASH SOLUTION

An aqueous wash solution was prepared containing TRITON TM X-100 nonionic surfactant (0.1 weight %), ethanolamine hydrochloride (0.26 molar, Sigma Chemical) and preservative (0.01 weight %), with the pH adjusted to 10.75 with 12 normal sodium hydroxide.

PHOSPHATE BUFFERED SALINE SOLUTION

This solution (0.05 molar) was prepared from sodium chloride (0.15 molar), sodium dihydrogen phosphate (0.01 molar) and sodium hydrogen phosphate (pH 7.2, 0.04 molar).

BLOCKING COMPOSITION

An aqueous blocking composition was prepared comprising α-casein (0.5 weight %), TWEEN 20 nonionic surfactant (tradename, 0.1 weight %), p-methoxyphenol (100 mmolar) and preservative (0.01 weight %).

A disposable test device, having three test wells and similar to that described in copending U.S. Ser. No. 98,248 (noted above), was used in the assay. The test devices had uncoated nylon microporous membranes BIODYNE TM A, microporous membrane from Pall Corp.) in each test well.

EXAMPLE 1

Extraction Composition

An extraction composition of the present invention was prepared by mixing the following components in water: NONIDCT NP-40 nonionic surfactant (5 weight %, tradename of Sigma Chemical), sodium deoxycholate (0.75 weight %, Sigma Chemical), sodium dodecyl sulfate anionic surfactant (0.4 weight %, Bio-Rad) and sodium chloride (1 molar). The pH of the composition was adjusted to 10.75 with 12 normal sodium hydroxide.

EXAMPLE 2

Assay for HSV-1 and HSV-2

This example illustrates the method of this invention using patient specimens containing either or both HSV-1 and HSV-2. Specimens were obtained from various patients from several clinics and hospitals using two swabs for each patient. One swab was used to practice this invention in a SURECELL TM test device at the clinic or hospital, and the second swab was used for a confirmatory test using standard culture techniques.

The first swabs from each patient were placed in extraction tubes and the extraction composition of Example 1 (1 ml) was added. The swabs were swirled in the extraction solution for 1-2 minutes after which the resulting extract was prefiltered through a filter device [composed of a polyester plug as a top layer, a 10 μm HDC (tradename, Pall Corp.) in the middle and a 5 μm LOPRODYNE TM microporous filter membrane (Pall Corp.) on the bottom]. This device is described in more detail in copending U.S. Ser. No. 308,842 filed by Hinckley et al on even date herewith and entitled, "Multiple Level Filter Device and Kit Containing Same, now U.S. Pat. No. 4,948,561 (issued Aug. 14, 1990)".

The prefiltered extract (200 μl) was then placed into each well of each test device allowing any HSV antigen to adsorb to the membrane in the well.

The test wells were washed with the wash solution noted above (120 μl), and the hydrogen peroxide solution (120 μl) noted above was added to each to remove any nonspecific oxidases. The wells were washed again (120 μl) with the wash solution. A sample (40 μl) of the labeled anti-creatine kinase conjugate (3 μg/ml) in the blocking composition described above was added to the negative control well of each test device. A sample (40 μl) of the anti-HSV conjugate was added to the other two wells of each device.

After 5 minutes incubation at room temperature to allow antibody-antigen complexation, the wells were washed twice with the wash solution described above (200 μl each time).

The leuco dye composition (40 μl) noted above was added to each test well, and after 5 minutes incubation at room temperature, the presence of reddish dye on the membrane was evaluated as an indication of the presence of HSV antigen in the specimen. For the patient samples tested, the sensitivity (true positives divided by the sum of true positive and false negatives) was 83%, and the specificity (true negatives divided by the sum of true negatives and false positives) was 100%. All positive results of the method were confirmed by the culture results.

EXAMPLE 3

Comparative Example at Various pHs

This example compares the practice of the present invention to a similar method in which the extraction composition was buffered at low pH (less than 8.5).

MATERIALS

SURECELL ™ test devices were used containing 5 μm nylon microporous membranes (Pall Corp.) in each of the test wells.

Aqueous extraction compositions of this invention were prepared from NONIDET NP40 nonionic surfactant (5 weight %), sodium dodecyl sulfate (0.5 weight %) and deoxycholate (1 weight %) in ethanolamine hydrochloride (0.26 molar). The pH of the extraction compositions were from 9 to 12. A Control extraction composition was similarly prepared having a pH of 7.0 in phosphate buffered saline solution.

A wash solution was prepared comprising ethanolamine hydrochloride (0.26 molar), TWEEN 20 nonionic surfactant (tradename, 0.1 weight %) and preservative (0.01 weight %). The pH was raised to 10.7 using 12 normal sodium hydroxide.

The other compositions and solutions used were those described above.

ASSAY

Test samples containing HSV-1 antigen and interferents were prepared from the following: whole blood (25 μl), HL-60 cells ($5 \times 10^7$ cells/ml, ATCC CCL-240, 50 μl), HEP-2 cells ($10^4$ cells/ml, 5 μl, ATCC CCL-23), porcine mucin (200 μl, Sigma Chemical) and HSV-1 antigen in phosphate buffered saline solution (0.1 mg/ml bovine serum albumin, 100 μl), 1:4000 dilution added to the test wells.

A background sample was prepared containing only the interferents.

Both test and background samples (65 μl) were mixed with each of the extraction compositions (925 μl). After 1-2 minutes incubation at room temperature, the solutions were prefiltered and added to the test wells of the test devices (200 μl per well).

The wash solution (200 μl) was added to each well, followed by addition of the hydrogen peroxide solution (120 μl). A second wash (120 μl) was then applied to each well.

The peroxidase-labeled anti-HSV (1.8 μg/ml) was added in the blocking composition to each well, followed by incubation at room temperature for 5 minutes.

After another wash (200 μl), the leuco-dye providing composition (40 μl) was added. After another 5 minutes incubation at room temperature, the dye density on each membrane was measured by transmission density ($D_T$). The results are shown in the following Table I. It is apparent that when using a low pH extraction composition, there was no flow through the test device membranes. Thus, the assays could not be performed. However, good sensitivity and flow through were obtained with the extraction compositions of this invention having a pH ranging from 9 to 12.

TABLE I

| Extraction Solution (pH) | $D_T$ Test Sample | $D_T$ Background Sample |
|---|---|---|
| Control (7.0) | —* | —* |
| Example 3 (9.0) | 0.198 | 0.023 |
| Example 3 (10.4) | 0.235 | 0.033 |
| Example 3 (12.0) | 0.156 | 0.023 |

*No fluid flow was obtained through the membrane. The membrane became clogged, resulting in no test.

EXAMPLE 4

Comparison Using Various Surfactants in the Extraction Composition

This example demonstrates the importance of having all critical components of the extraction composition in order to obtain the desired membrane flow through and sensitivity in a herpes assay.

MATERIALS

SURECELL ™ test devices were used having certain polymeric beads [2 μm, poly(styrene-co-m and p-chloromethylstyrene), 0.1% solids in phosphate buffered saline solution] added to the test wells.

Aqueous extraction compositions were prepared as follows:

A composition of this invention containing sodium dodecyl sulfate (0.1 weight %), deoxycholate (0.2 weight %), NONIDET NP40 nonionic surfactant (tradename, 1 weight %) and ethanolamine hydrochloride (0.26 molar) and having a pH of 9.

Control composition A containing only sodium dodecyl sulfate (1.3 weight %) and ethanolamine hydrochloride (0.26 molar) and having a pH of 9.

Control composition B containing only deoxycholate (1.3 weight %) and ethanolamine hydrochloride (0.26 molar) and having a pH of 9.

Control composition C containing only NONIDET NP40 nonionic surfactant (1.3 weight %) and ethanolamine hydrochloride (0.26 molar) and having a pH of 9.

A wash solution was prepared having ethanolamine hydrochloride (0.26 molar) and TWEEN 20 nonionic surfactant (tradename, 1 weight %) and a pH of 10.4 provided by 12 normal sodium hydroxide.

Test samples containing antigen were prepared from HSV cell lysate noted above (10 μl), and diluted 1:40 in phosphate buffered saline solution containing bovine serum albumin (0.1 mg/ml). A 1:4000 dilution was added to each test well.

Background samples containing the following interferents were prepared: whole blood (25 μl/ml), porcine mucin (20 μl/ml), HL-60 cells (5 μl/ml) and HEP-2 cells (5 μl/ml) in phosphate buffered saline solution (80 μl/ml of extracted solution).

Other solutions and compositions used were like those described above in Example 1.

ASSAY

Test samples and background samples (135 μl) were added to each of the extraction compositions (865 μl) and mixed at room temperature for 5 minutes. After prefiltration of the resulting mixtures, each one (200 μl) was added to each test well, followed by washing (200 μl). The hydrogen peroxide solution (120 μl) was then added to each test well followed another wash (200 μl).

After addition of the peroxidase-labeled anti-herpes conjugate (40 μl), the test devices were incubated for 5 minutes at room temperatute. Another wash (400 μl) was carried out, and the leuco dye-providing composition (80 μl) was added to each test well. Incubation at room temperature for 5 minutes followed. Dye formation was stopped by the addition of sodium azide (80 μl, 0.1 weight %), and the $D_T$ was measured. The results are shown in Table II below. These results indicate that only with all of the critical components in the extraction can good flow through and sensitivity be obtained.

TABLE II

| Extraction Solution | Flow Through | DT Test Sample | Background Sample |
|---|---|---|---|
| Example 4 | Fast | 0.134 | 0.014 |
| Control A | Fast | 0.033 | 0.017 |
| Control B | Slow | 0.111 | 0.017 |
| Control C | Very Slow | 0.157 | 0.011 |

The invention has been described in detail with particular reference to preferred embodiments thereof, but it will be understood that variations and modifications can be effected within the spirit and scope of the invention.

I claim:

1. An extraction composition useful for extracting an antigen from herpes simplex virus, said composition having a pH of from about 8.5 to about 12, and comprising an alcoholamine or a salt thereof, a nonionic surfactant comprised of a condensation product of an alkylphenol and ethylene oxide, cholic acid or a derivative or salt thereof and an anionic surfactant.

2. The composition of claim 1 having a pH of from about 9 to about 11.

3. The composition of claim 1 said anionic surfactant comprises an alkyl sulfate anion and an alkali metal or ammonium cation, said alkyl having from 6 to 12 carbon atoms.

4. The composition of claim 1 wherein said nonionic surfactant has from 5 to 35 ethylene oxide groups and 6 to 10 carbon atoms in the alkyl group.

5. The extraction composition of claim 1 further comprising an inorganic salt.

6. The extraction composition of claim 5 having a pH of from about 9 to about 11, and comprising ethanolamine or a salt thereof, a nonionic surfactant having 9 or 10 ethylene oxide groups and an octyl group on the phenol nucleus, deoxycholic acid or sodium deoxycholate, an anionic surfactant which is sodium dodecyl sulfate or sodium decyl sulfate and sodium chloride as said inorganic salt.

7. A method for extracting a glycoprotein antigen from herpes simplex virus comprising:
A. providing a specimen suspected of containing herpes simplex virus, and
B. contacting said specimen with an extraction composition having a pH of from about 8.5 to about 12, and comprising an alcoholamine or a salt thereof, a nonionic surfactant comprised of a condensation product of an alkylphenol and ethylene oxide, cholic acid or a derivative or salt thereof and an anionic surfactant under conditions and for at time sufficient to extract said antigen.

8. The method of claim 7 wherein said extraction composition further compriese an inorganic salt.

9. The method of claim 7 wherein said extraction composition has a pH of from about 9 to about 11.

10. The method of claim 8 wherein said extraction composition has a pH of from about 9 to about 11, and comprising ethanolamine or a salt thereof, a nonionic surfactant having 9 to 10 ethylene oxide groups and an octyl group on the phenol nucleus, deoxycholic acid or sodium deoxycholate, an anionic surfactant which is sodium dodecyl sulfate or sopdium decyl sulfate and sodium chloride as said inorganic salt.

11. A method for the determination of herpes simplex virus comprising:
A. extraction a herpes simplex viral antigen from a specimen suspected of containing herpes simplex virus with an extraction composition having a pH of from about 8.5 to about 12, and comprising an alcoholamine or a salt thereof, a nonionic surfactant comprised of a condensation product of an alkylphenol and ethylene oxide, cholic acid or a derivative or salt thereof and an anionic surfactant.
B. contacting said extracted antigen with herpes simplex viral antibodies to form an immunological complex, and
C. determining the presence of said complex as an indication of thepresence of herpes simplex virus in said specimen.

12. The method of claim 11 wherein said herpes simplex viral antibodies are labeled for detection.

13. The method of claim 12 wherein sid herpes simplex viral antibodies are labeled with an enzyme.

14. The method of claim 11 wherein said herpes simplex viral antibodies are unlabeled and said antibody-antigen complex is determined using an anti-antibody which is labeled for detection.

15. The method of claim 11 wherein said extraction composition further comprises an inorganic salt.

16. The method of claim 11 carried out in whole or part using a disposabloe test device comprising a microporous membrane for separating said immunological complex from uncomplex materials.

17. The method of claim 11 wherein said extraction composition has a pH of from about 9 to about 11.

18. The method of claim 15 wherein said extraction composition has a pH of from about 9 to about 11, and comprises ethanolamine or a salt thereof, a nonionic surfactant having 9 or 10 ethylene oxide gorups and an octyl group on the phenol nucleus, deoxycholic acid or sodium deoxycholate, and anionic surfactant which is sodium dodecyl sulfate or sodium decyl sulfate and sodium chloride as said inorganic salt.

19. The method of claim 11 for the determination of both herpes simplex virus-1 and herpes simplex virus-2.

20. A diagnostic test kit useful for the determination of herpes simplex virus comprising:
(a) an extraction composition having a pH of from about 8.5 to about 12, and comprising an alcoholamine or a salt thereof, a nonionic surfactant comprised of a condensation product of an alkylphenol and ethylene oxide, cholic acid or a derivative or salt thereof and an anionic surfactant, and (b) antibodies directed to a herpes simplex viral antigen.

21. The test kit of claim 20 wherein said antibodies are labeled with an enzyme.

22. The test kit of claim 21 further comprising a composition providing a dye in the presence of said enzyme.

23. The test kit of claim 20 wherein said extraction composition further comprises an inorganic salt.

24. The test kit of claim 20 further comprising a disposable test device having at least one test well in which a microporous membrane is mounted.

* * * * *